United States Patent

Lattin et al.

[11] Patent Number: 5,919,155
[45] Date of Patent: Jul. 6, 1999

[54] ELECTROTRANSPORT SYSTEM HAVING FLEXIBLE CONNECTOR MEANS

[75] Inventors: Gary A. Lattin, Forest Lake, Minn.; J. Richard Gyory, San Jose, Calif.; Charles Albert, San Francisco, Calif.; Scott Jay Gilbert, Cupertino, Calif.

[73] Assignee: ALZA Corporation, Palo Alto, Calif.

[21] Appl. No.: 08/374,006

[22] Filed: Jan. 18, 1995

Related U.S. Application Data

[63] Continuation-in-part of application No. 07/999,206, Dec. 31, 1992, abandoned.

[51] Int. Cl.[6] .................................................. A61N 1/30
[52] U.S. Cl. .............................. 604/20; 439/909; 607/149
[58] Field of Search ........................... 439/29, 592, 840, 439/909; 604/20–21; 607/115, 148, 149, 152

[56] References Cited

U.S. PATENT DOCUMENTS

| | | |
|---|---|---|
| 2,667,162 | 1/1954 | Zwahlen . |
| 2,784,715 | 3/1957 | Kestler ................................ 128/172.1 |
| 3,412,731 | 11/1968 | Reynolds . |
| 3,472,233 | 10/1969 | Sarbacher .............................. 128/422 |
| 3,677,268 | 7/1972 | Reeves ................................ 128/172.1 |
| 4,406,658 | 9/1983 | Lattin et al. ............................. 604/20 |
| 4,457,748 | 7/1984 | Lattin et al. ............................. 604/20 |
| 4,474,570 | 10/1984 | Ariura et al. ............................. 604/20 |
| 4,543,958 | 10/1985 | Cartmell ............................... 607/148 |
| 4,708,716 | 11/1987 | Sibalis . |
| 4,752,285 | 6/1988 | Petelenz et al. ......................... 604/20 |
| 4,786,278 | 11/1988 | Masaki . |
| 4,856,188 | 8/1989 | Sibalis . |

FOREIGN PATENT DOCUMENTS

| | | | |
|---|---|---|---|
| A750187 | 10/1985 | Australia ........................ A61N 1/00 |
| 0461680A2 | 12/1991 | European Pat. Off. ......... A61N 1/30 |
| 0513879A2 | 11/1992 | European Pat. Off. ....... A61M 37/00 |
| 0447549 | 1/1913 | France . |
| 410009 | 5/1934 | United Kingdom . |
| 160427 | 12/1985 | United Kingdom ............. A61N 1/04 |
| WO8807392 | 10/1988 | WIPO .............................. A61N 1/04 |

*Primary Examiner*—Mark Bockelman
*Attorney, Agent, or Firm*—D. Byron Miller; Steven F. Stone

[57] ABSTRACT

A device (10) for the electrically assisted delivery of a therapeutic agent is described. The device (10) has rigid zones or regions (12, 14) which are physically connected by a flexible means (16) such as a web. The flexible means (16) permits the rigid zones (12, 14) to move independently with respect to each other while remaining physically connected or coupled. In a preferred embodiment, the rigid zones are physically and electronically coupled by the flexible means. In another embodiment, the device (500) comprises one or more rigid zones, the skin side of the rigid zone having a radius of curvature (520) which approximates that of the body site to which the device (500) is to be attached. A method of increasing the body surface conformability of an electrotransport device (50, 150, 170) is described. The method involves the step of intentionally placing rigid subcomponents (58, 36, 37) of the device in physically separate zones (52, 54; 152, 154, 156, 158; 172, 174, 176, 178) within the device. The rigid zones (52, 54; 152, 154, 156, 158; 172, 174, 176, 178) are separate and are coupled by flexible connector means (56, 62; 160, 162). In this manner, a conformable mosaic of rigid zones which comprises the device is created.

20 Claims, 12 Drawing Sheets

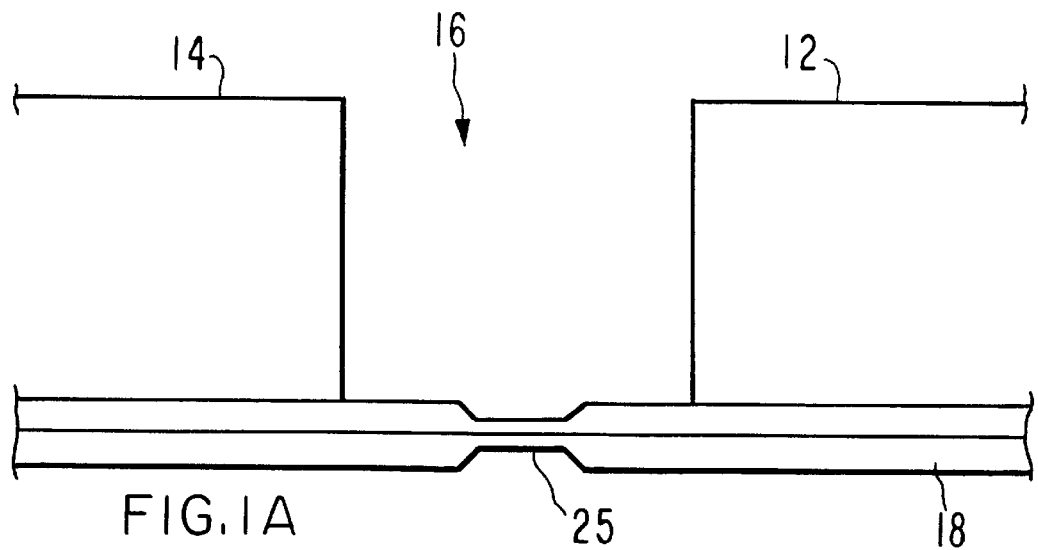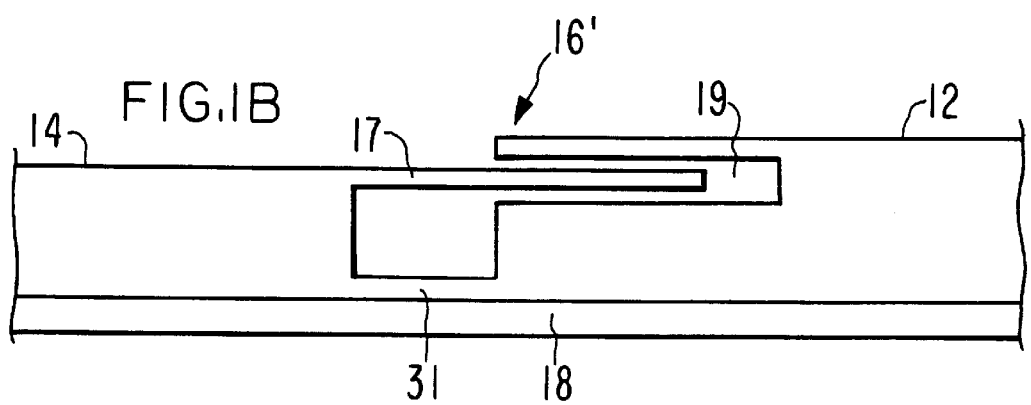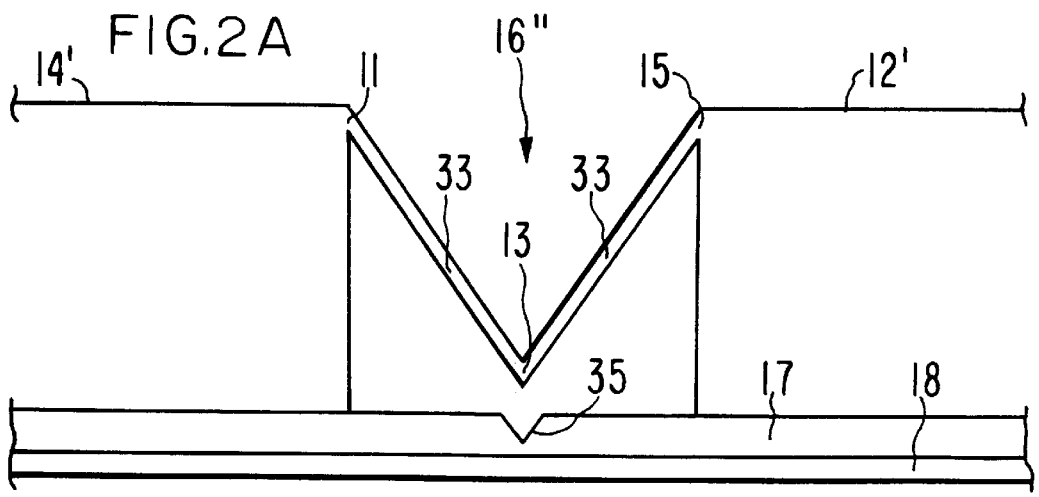

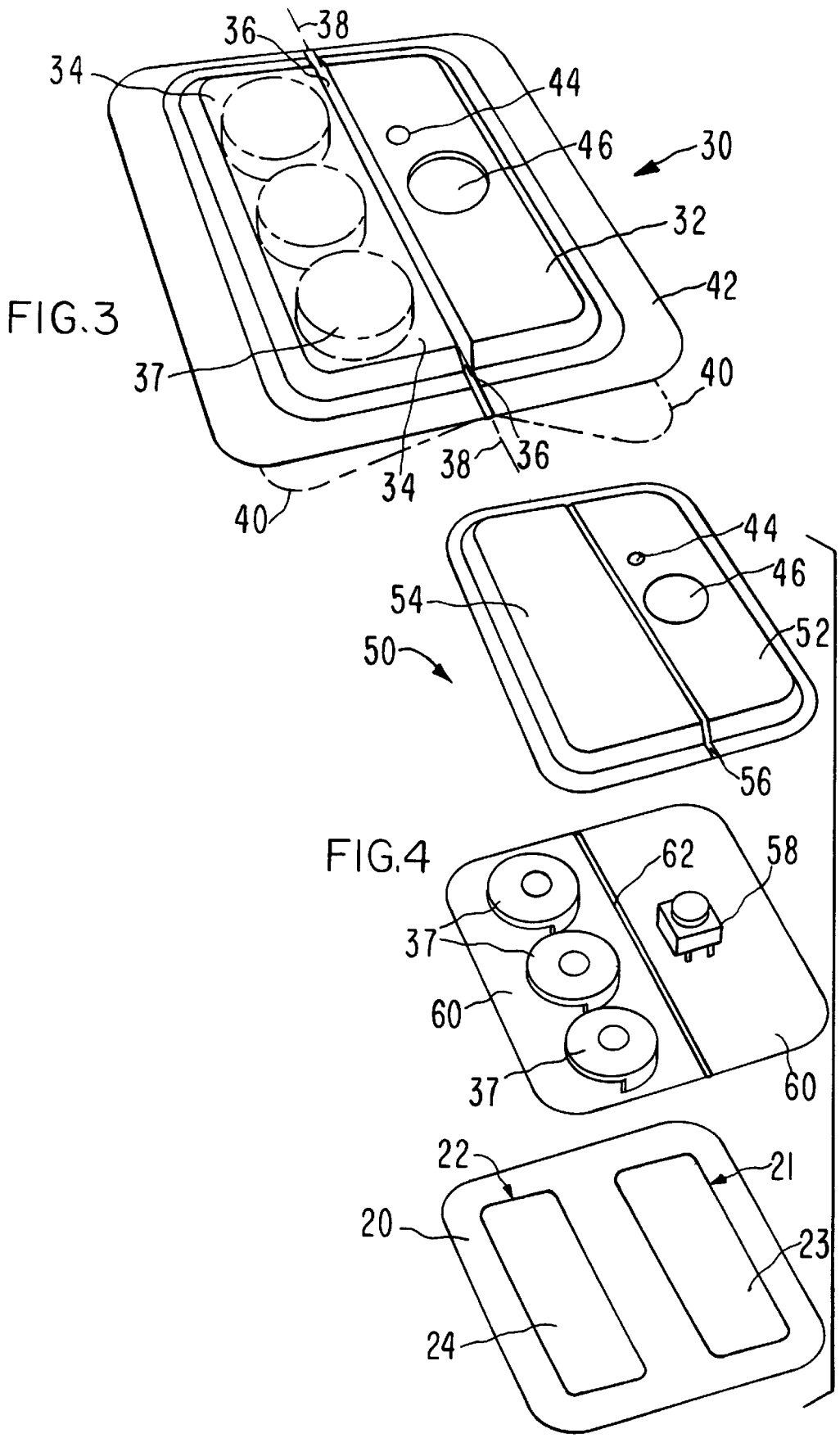

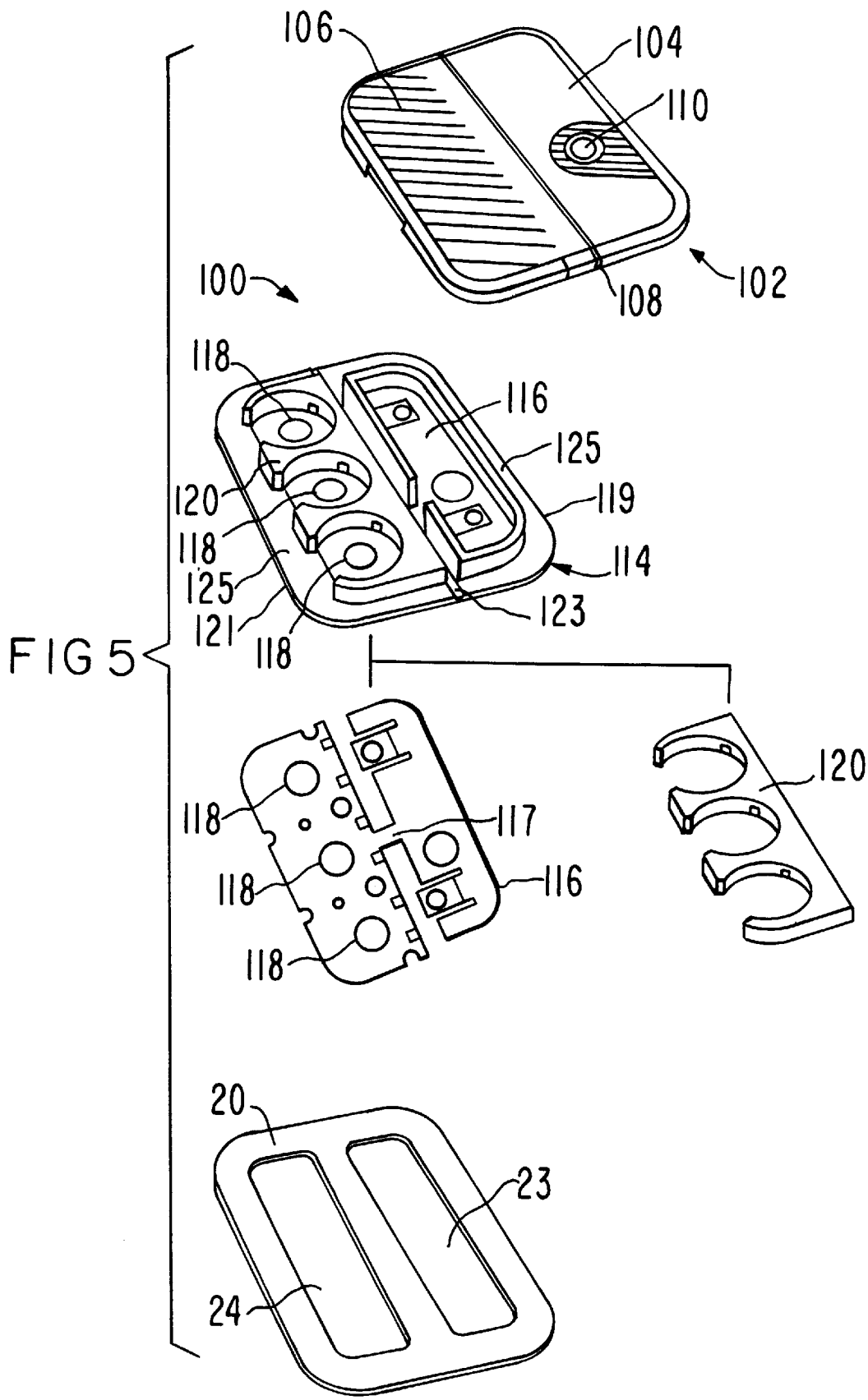

ELECTROTRANSPORT SYSTEM HAVING FLEXIBLE CONNECTOR MEANS

This is a continuation-in-part of U.S. patent application Ser. No. 07/999,206 filed Dec. 31, 1992 now abandoned.

TECHNICAL FIELD

This invention generally concerns apparatuses for the electrically assisted delivery of a therapeutic agent. Such apparatuses are referred to broadly herein as electrotransport devices.

More specifically, this invention relates to electrotransport drug delivery devices in which active species or drugs are directly or indirectly delivered through the skin of a patient by application of electromotive force. Yet more specifically, this invention relates to electrotransport devices having physically coupled, substantially rigid zones or regions wherein the means of coupling permits the zones or regions to be planar or non-planar and thereby to conform to complex, curved and non-planar surfaces. Yet even more specifically, this invention relates to electrotransport devices, such as iontophoresis devices, having physically and electrically coupled rigid zones or regions which are maintained in intimate contact with a patient's skin so as to deliver, transdermally, drug or therapeutic agent.

BACKGROUND ART

The present invention concerns apparatuses for transdermal delivery or transport of therapeutic agents, typically through iontophoresis. Herein the terms "electrotransport", "iontophoresis", and "iontophoretic" are used to refer to methods and apparatus for transdermal delivery into the body of therapeutic agent, whether charged or uncharged, by means of an applied electromotive force to an agent-containing reservoir. The particular therapeutic agent to be delivered may be completely charged (ie, 100% ionized), completely uncharged, or partly charged and partly uncharged. The therapeutic agent or species may be delivered by electromigration, electroosmosis, electroporation or a combination of these. Electroosmosis has also been referred to as electrohydrokinesis, electro-convection, and electrically-induced osmosis. In general, electroosmosis of a therapeutic species into a tissue results from the migration of solvent, in which the species is contained, as a result of the application of electromotive force across the therapeutic species reservoir-tissue interface.

As used herein, the terms "iontophoresis" and "iontophoretic" refer to (1) the delivery of charged drugs or agents by electromigration, (2) the delivery of uncharged drugs or agents by the process of electroosmosis, (3) the delivery of charged drugs or agents by the combined processes of electromigration and electroosmosis, (4) the delivery of a mixture of charged and uncharged drugs or agents by the combined processes of electromigration and electroosmosis, and/or (5) the delivery of charged or uncharged drug(s) or agent(s) by the combined processes of electromigration, electroosmosis, and electroporation.

Iontophoretic devices for delivering ionized drugs through the skin have been known since the early 1900's. Deutsch U.S. Pat. No. 410,009 (1934) describes an iontophoretic device which overcame one of the disadvantages of such early devices, namely that the patient needed to be immobilized near a source of electric current. The Deutsch device was powered by a galvanic cell formed from the electrodes and the material containing the drug to be transdermally delivered. The galvanic cell produced the current necessary for iontophoretically delivering the drug. This device allowed the patient to move around during iontophoretic drug delivery and thus imposed substantially less interference with the patient's daily activities.

In presently known iontophoresis devices, at least two electrodes are used. Both of these electrodes are disposed so as to be in intimate electrical contact with some portion of the skin of the body. One electrode, called the active or donor electrode, is the electrode from which the ionic substance, agent, medicament, drug precursor or drug is delivered into the body via the skin by iontophoresis. The other electrode, called the counter or return electrode, serves to close the electrical circuit through the body. In conjunction with the patient's skin contacted by the electrodes, the circuit is completed by connection of the electrodes to a source of electrical energy, eg, a battery; and usually to circuitry capable of controlling current passing through the device. For example, if the ionic substance to be driven into the body is positively charged, then the positive electrode (the anode) will be the active electrode and the negative electrode (the cathode) will serve to complete the circuit. If the ionic substance to be delivered is negatively charged, then the cathodic electrode will be the active electrode and the anodic electrode will be the counter electrode. In some instances, the drug may be formulated such that in one formulation the drug ions are positively charged and in a second formulation the drug ions are negatively charged. In such situations, the positively charged drug ions may be delivered from the anode and/or the negatively charged drug ions may be delivered from the cathode. Hence, drug delivery may occur from one or both electrodes and may occur simultaneously as well as sequentially.

Furthermore, existing iontophoresis devices generally require a reservoir or source of the beneficial agent or drug, preferably an ionized or ionizable species (or a precursor of such species) which is to be iontophoretically delivered or introduced into the body. Such drug reservoirs are connected to the anode or the cathode of an iontophoresis device to provide a fixed or renewable source of one or more desired species or agents.

Perhaps the most common use of iontophoresis today is in diagnosing cystic fibrosis by delivering pilocarpine transdermally. Iontophoretically delivered pilocarpine stimulates sweat production, the sweat is collected, and is analyzed for its chloride ion content. Chloride ion concentration in excess of certain limits suggests the possible presence of the disease.

Electrotransport devices generally contain an electronic circuit which controls the current output of the device. In more recent years, the size of electrotransport devices has been reduced to a point where the devices can be mounted and worn on the skin. In order to protect, adequately, the electronic circuitry in such skin-mounted devices and for a variety of other reasons, these devices have generally utilized a substantially rigid container or assembly. See for example Lattin et al, U.S. Pat. No. 4,406,658 (FIGS. 2 and 3) and Lattin et al, U.S. Pat. No. 4,457,748 (FIGS. 1, 3 and 4). While these rigid devices were acceptable in those applications (eg, cystic fibrosis diagnosis) which required the patient to wear the device for only a short period of time, ie, on the order of 30 minutes or less, these devices have been found to be somewhat uncomfortable in those applications where the patient must wear the device for periods longer than an hour. Particularly in applications where the patient must wear the device for an extended period of time (eg, days, weeks or months) comfort is a significant issue.

In response to these difficulties, the advantages of developing a flexible electrotransport delivery device were recognized. For example, Ariura et al, U.S. Pat. No. 4,474,570, discloses one example of a flexible iontophoresis device. This device utilizes electrode assemblies comprised of a current distributing conductive layer, a drug or electrolyte salt-containing gel layer and a thin backing layer, all laminated together. The Ariura device utilizes minimal electronic circuitry, specifically only a single button cell battery which is connected though a flexible lead wire to an electrode assembly. In order to make the device completely flexible, Ariura utilizes thin "sheet" batteries which have a thickness of only about 0.5 to 2 mm. Because the Ariura et al device is completely flexible, it is able to conform to many irregular body surfaces and can be worn comfortably for longer periods of time. While flexible iontophoretic delivery devices, such as that disclosed by Ariura et al represent a significant advantage over rigid devices, in terms of comfort for the wearer, they present other disadvantages. For example, the Ariura et al device is very limited in terms of the electronic circuitry which may be utilized in the device and yet still retain its flexible characteristics. Furthermore, there are many iontophoretic drug delivery applications which the current requirements are too high for the single small battery disclosed in the Ariura et al device. If multiple batteries are placed in the Ariura et al device, the device becomes substantially nonflexible and thereby loses its comfort advantage.

In addition to batteries, electrotransport delivery devices may have other components which are themselves relatively rigid and inflexible (ie, one or more electrical components) or which require a relatively rigid housing in order to adequately protect the component during shipping and handling of the device. For example, "dry" electrotransport delivery devices which are hydrated immediately before use sometimes carry on-board water pouches. In order to adequately safeguard against premature hydration caused by inadvertent rupture of the on-board water pouches, it may be necessary to provide structural rigidity to the device at least in the vicinity of the water pouches. Other device components, eg, delicate electronics, may require at least portions of the electrotransport device to be relatively rigid to provide protection, electrical continuity or other function.

Unfortunately, devices having rigid regions generally do not conform well to the body site to which the device is attached, particularly when the means of attachment is a releasable contact adhesive. This can cause an electrotransport system to peel away from the body site, or to alternatively cause internal layers of the device itself to detach or delaminate and thereby fail. This invention allows an electrotransport drug delivery device having rigid regions to conform to the body surface (eg, to skin) to which it is adhesively held with a reduced tendency to peel away.

U.S. Pat. No. 4,752,285 to Petelenz discloses a wrist-disposed iontophoresis device held in place by a bracelet comprising an iontophoresis apparatus including a remote electrode. The iontophoresis apparatus and electrode of Petelenz U.S. Pat. No. '285 are connected by wires to a separate current source.

The present invention overcomes the problems encountered in the prior art and is not suggested or disclosed in the references alone or in combination.

DISCLOSURE OF THE INVENTION

Briefly, in one aspect, the present invention is an assembly or device for delivering an agent by electrotransport through a body surface. A device of this invention has at least two rigid regions which are adapted to be maintained in ion-transmitting relationship with the body surface at spaced apart locations, and which are held in their spaced apart locations preferably by means of biocompatible adhesive. Despite substantial rigidity, at least a drug delivery component of the assembly of this invention is maintained in intimate, drug-transmitting relation with the body surface. A device of this invention further includes a flexible connector means which physically connects the rigid regions but which permits the rigid regions to move with respect to each other during agent electrotransport without loss of intimate contact with the surface of the patient's body. Specific embodiments of flexible connector means of this invention include hinges and flexible polymeric webs.

In a preferred practice of this invention, the flexible connector means both (1) physically connects or couples the rigid zones to one another; and (2) electronically connects a component in one of the rigid zones to a component in the other rigid zone. Generally, this means that a flexible electronic conductor comprises a part of the flexible connector means. More preferably, the flexible connector means physically connects the donor and counter electrodes of the electrotransport delivery device. Most preferably, the flexible connector means is extendable, thereby allowing the zones (eg, the electrodes) to be placed at closely adjacent locations or more spaced apart locations on the patient's body.

In a preferred practice, the rigid components or zones of the assembly of this invention are held in intimate, ion-transmitting relation to a portion of a patient's body by means of a biocompatible adhesive.

In yet another preferred practice, a device of this invention has a plurality of rigid zones and a plurality of flexible connector means physically or physically and electronically coupling the rigid zones.

In a further preferred practice of this invention, the rigid regions are contoured to the body surface to which they are applied.

Preferably, the rigid regions have a flexural rigidity, EI, greater than about $1.5 \times 10^{-3}$ kg-m$^2$/rad and the flexible connector means has a flexural rigidity of less than about $0.75 \times 10^{-3}$ kg-m$^2$/rad. More preferably, the rigid regions have a flexural rigidity of greater than about $5.0 \times 10^{-3}$ kg-m$^2$/rad and the flexible connector means has a flexural rigidity of less than about $0.45 \times 10^{-3}$ kg-m$^2$/rad. Most preferably, the rigid regions have a flexural rigidity of greater than about $15 \times 10^{-3}$ kg-m$^2$/rad and the flexible connector means has a flexural rigidity of less than about $0.15 \times 10^{-3}$ kg-m$^2$/rad. In addition, the difference between the flexural rigidity of a rigid region and the flexural rigidity of the flexible connector means ($\Delta$EI) is preferably greater than about $0.3 \times 10^{-3}$ kg-m$^2$/rad, more preferably greater than about $1.5 \times 10^{-3}$ kg-m$^2$/rad, and most preferably greater than about $5.0 \times 10^{-3}$ kg-m$^2$/rad.

The flexural rigidity of a rigid zone and/or a flexible connector means is measured in accordance with the test method described in connection with FIG. 12, hereinafter.

BRIEF DESCRIPTION OF THE DRAWINGS

The present invention may be better understood with reference to the detailed description below and the attached drawings in which like numerals are used to refer to like features throughout and in which:

FIG. 1A is an enlarged side view of the flexible connector means 16 shown in FIG. 1;

FIG. 1B is a side view of an alternate connector means 16' which can be used in place of flexible connector means 16 shown in FIG. 1A.

FIG. 2A is an enlarged partial section side view of its flexible connector means 16" shown in FIG. 2.

FIG. 3 is a perspective view of another embodiment of the present invention;

FIG. 4 is an exploded view of the components of the device shown in FIG. 3;

FIG. 5 is an exploded, perspective view of another embodiment of this invention;

MODES FOR CARRYING OUT THE INVENTION

Figure 1:
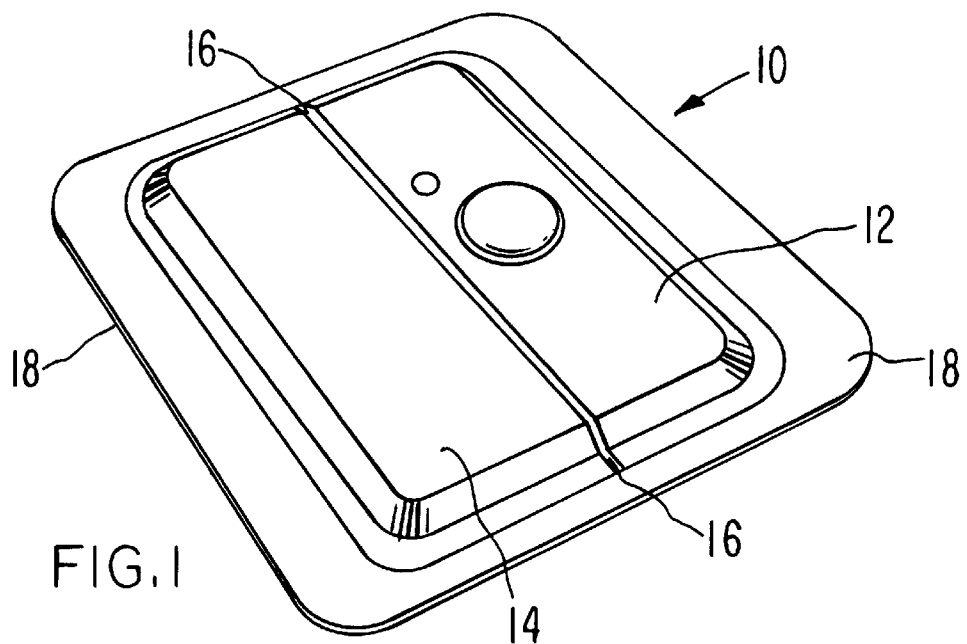
FIG. 1 is a perspective view of one embodiment of the present invention.

Thus there is shown, in FIG. 1, a perspective view of an electrotransport device or assembly 10 of this invention. Electrotransport device 10 comprises two rigid (as defined herein) housings or subassemblies 12, 14 connected by flexible connector means 16. Housings 12 and 14 each comprise rigid zones or region, which rigid zones or regions are physically connected to one another by flexible connector means 16. Device 10 includes a flexible, biocompatible or skin compatible adhesive sheet 18 which preferably extends beyond the outer perimeter of housings 12, 14. By making the area of adhesive sheet 18 larger than the area of housings 12, 14 there is greater area of contact between sheet 18 and a patient's skin resulting in more secure attachment of the device 10 thereto. The extension of the peripheral edges of flexible sheets 18 beyond the peripheral edges of rigid housings 12, 14 also permits a more gentle transition between the patient's skin and rigid housings 12, 14, thereby making device 10 more comfortable to wear.

The rigid housings 12, 14 may contain, for example, electrical circuit components which are coupled through eg, flexible hinge 16. The circuit components are mounted (and protected) in the two rigid housings 12, 14. These housings are preferably comprised of a substantially thermoplastic, rigid material. The housings 12, 14, themselves, are substantially incapable of conforming to the contour of the underlying skin surface and, but for hinge 16, would eventually cause the underlying adhesive sheet 18, (which contains a typical skin contact adhesive) either to peel away from the skin, or pull on the skin and thereby cause discomfort for the wearer as a result of normal body movement.

In FIG. 1A there is shown a detail of the flexible connector 16 which physically (and preferably) electronically couples or connects rigid housings 12, 14. Connector 16 comprises a base 17 on which adhesive 18 is located. Base 17 and adhesive 18 have a zone, line, or means of flex which in this example is simply a "necked down" region or portion 25 of the support member. The necked down segment 25 is more flexible than the rest of the support structure. Alternatively a cross-sectioned "V" segment could be used in place of the "necked down" region shown to provide the increased flexibility or flex zone, region or line. Segment 25 permits rigid zones 12, 14 to move independently with respect to each other while maintaining their physical proximity. Base 17 may further comprise flexible electronic coupler means. This embodiment of the invention is discussed below. Base 17 may or may not contain flexible circuitry depending upon the rest of the device construction. In the embodiment shown base 17 contains flexible electrical connector or circuitry (not shown).

Another example of a flexible connector means which can be used flexibly to connect rigid housings 12, 14 is hinge 16' shown in FIG. 1B. Hinge 16' is formed by inserting flexible fin 17 into recess 19 in housing 12. Fin 17 is slidably received in recess 19, allowing fin 17 to slide in and out of recess 19 as housings 12, 14 are flexed about hinge 16'. Thin, flexible zone 31 provides a region or area which permits housings 12, 14 to bend or flex with respect to each other. Those skilled in the flexible hinge art will readily appreciate that any number of hinge designs may be used in place of the specific designs illustrated in FIGS. 1A, 1B and 2A.

The terms "rigid" and "flexible" are used to describe not only housings 12, 14, and hinge 16, respectively, but are also used extensively elsewhere herein. The term "rigid" when used in describing a portion or zone of an electrotransport system means that the portion or zone has sufficient stiffness so as to be incapable of adhering to a body surface (eg, to skin) of a patient using a biocompatible and pharmaceutically acceptable contact adhesive without injury to the body surface or identifiable patient discomfort, throughout the normal range of body motion. In other words, a "rigid" zone of an electrotransport system is prone to peel from the skin, or alternatively to undergo delamination of adjacent layers within the rigid zone of the system, thereby interfering with the desired agent or drug delivery protocol.

The term "flexible" when used to describe the flexible means which connects the rigid zones of an electrotransport system means having sufficient flexibility so as to enable the "rigid" portions or zones of the system to be capable of adhering to the body surface, by means of a biocompatible, pharmaceutically acceptable contact adhesive without injury to the body surface or identifiable patient discomfort, throughout the normal range of body motion and for the time period in which drug or agent is to be delivered.

Those skilled in the art may readily determine the flexibility or rigidity of a particular component or zone in an electrotransport system by using the following test method. Although any number of stress-strain testing apparatus may be used to determine flexural rigidity, one preferred apparatus is an Instron stress-strain testing machine Model No. 1122 which may be used interchangeably with a number of different tension load cells. A preferred load cell for testing the flexible connector means of the present invention is the Instron 2000 gm tension load cell Model No. A30-38(A). A preferred tension load cell for measuring the flexural rigidity of the rigid zones according to the present invention is an Instron 500 kg tension load cell. A tension load cell used to determine the parameters used in this application is described below with reference to FIG. 12.

Figure 2:
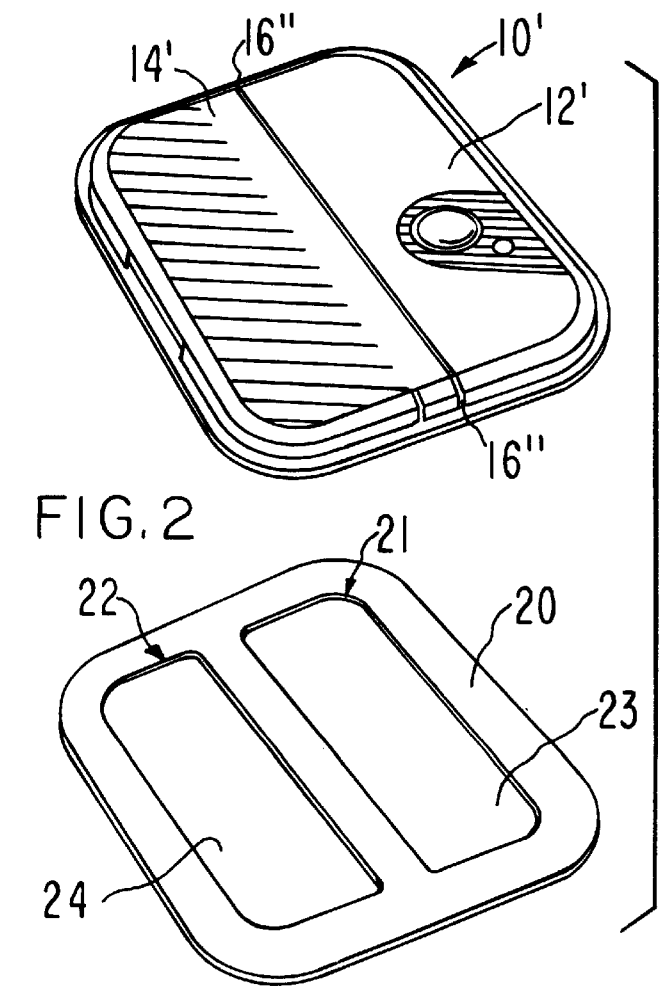
FIG. 2 is an exploded view of a second embodiment of the present invention similar to that of FIG. 1

FIG. 2 shows an exploded view of an electrotransport delivery device 10' of this invention in which the rigid housing 12' and 14' (which contain the battery(ies) and any associated electronic circuitry) are shown separated from a flexible sheet 20 which is secured to the underside of housings 12', 14' during use of device. Sheet 20 may be attached to the underside of housings 12' and 14' by conventional means, eg, an adhesive, rivets, or snap connectors (not shown in the figure) or combination of these attachment means. The skin contacting undersurface of sheet 20 may itself be tacky, (eg, tacky polyisobutylene) or may be coated with an appropriate biocompatible contact adhesive (eg, a silicone adhesive). In this manner, device 10' may be adhered to a patient's skin by flexible, biocompatible adhesive sheet 20. Sheet 20 is substantially the same size as the outer profile of housings 12', 14' and thus does not extend beyond the outer periphery of housings 12', 14'. Sheet 20 is preferably comprised of a material which is substantially impermeable to the passage of ions therethrough, eg, a hydrophobic adhesive material. Provided within the sheet 20 are wells 21 and 22 which contain a donor reservoir 23 containing the agent to be delivered and a counter reservoir 24 containing a biocompatible electrolyte salt. The reservoirs 23 and 24 are preferably comprised of a hydrophilic polymer (eg, a gel) matrix loaded with either the beneficial agent or the biocompatible electrolyte salt, respectively. Thus, each of reservoirs 23 and 24 contain an agent or salt, and preferably an ionizable agent or salt, which is suitable for delivery into the body. Sheet 20 is adapted to be secured to the bottom of housings 12' and 14' in a manner which electrically connects the reservoirs 23 and 24 with appropriate current conducting members within housings 12', 14' respectively.

Optionally, the upper or skin distal portion of device 10' (ie, housings, 12', 14' and all of the electronic components contained therein) is releasably attached to sheet 20, enabling the user to remove sheet 20, after the agent contained in reservoir 23 has been depleted, and replace it with a new sheet 20. In this manner, the upper portion of device 10' is reusable and the lower or skin proximal portion of device 10' (ie sheet 20) is adapted to be discarded after a single use and then replaced.

A flexible hinge 16" provides a flexible coupling between the two rigid zones comprising housings 12' and 14'. Components in housing 12' can be electronically connected to components in housing 14' across the flexible coupling of this invention eg, when the flexible connector means includes a flexible, conductive electronic circuit or component thereof. This is discussed in greater detail below.

One preferred example of a flexible coupler means or hinge 16 comprises a flexible plastic material, or what is sometimes referred to in this art as a "living hinge". A side view of such a hinge 16" is shown in partial section detail in FIG. 2A. The hinge 16" of FIG. 2A is a compound hinge comprised of a polymeric web 33 having three fold lines 11, 13 and 15. Fold lines 11, 13 and 15 are generally perpendicular to the plane of FIG. 2A. Adhesive 18 and base 17 also are shown in FIG. 2A. Base 17 has a relatively thinner flex zone or line 35 which, as shown, is a "V". Polymeric web 33 and flex line 35 permit rigid segments 12', 14' to bend with respect to each other. Web 33 and flex line 35 are aligned so that they can be flexed substantially in unison.

FIG. 3 shows an alternative, perspective embodiment of the invention. Electrotransport delivery device 30 includes two rigid zones comprised of rigid housings 32 and 34. Rigid housings 32, 34 contain batteries 37 (shown in phantom) and other electronic circuitry (not shown). Housing 32 optionally contains an indicator 44 and a bolus switch 46. Bolus switch 46, when activated by the patient or a medical professional, provides a higher level of electrical current for a predetermined or predeterminable period of time. This produces a correspondingly higher drug delivery over the predetermined time, providing a bolus of drug to the patient. Indicator 44 (an LED) provides an indication of whether the bolus is activated.

Housings 32, 34 are flexibly coupled by hinge 36 which flexes around imaginary axis 38. Thus in this embodiment, like devices 10 and 10', the flexible means flexes about an axis or line of flex. Housings 32, 34 bend or flex about hinge 36, from the substantially planar position shown to a non-planar position shown in phantom by reference numeral 40. The rigid, substantially planar housings 32, 34 are attached to an adhesive sheet 42 which is used to adhere device 30 to a body surface. Because of hinge 36, the rigid planar housings can be flexed about imaginary axis 38 in order to comfortably conform to a generally curved or contoured portion of a patient's body to which device 30 is attached via adhesive sheet 42.

FIG. 4 is an exploded view of a device 50 of the invention. As shown, device 50 includes two substantially rigid (eg, molded polypropylene) housings 52, 54 coupled by a flexible, uniaxial hinge 56. Rigid housing 52 houses one or more electronic circuit components 58 (eg, capacitors, transistors, an oscillators, or a pulse generator, etc), while rigid housing 54 houses batteries 37. The rigidity of both these case segments is dictated by functional concerns, eg, protection of internal components, and the rigidity of the internal components themselves.

As shown, circuit component 58 and batteries 37 are disposed on a flexible printed circuit board 60. Flexible printed circuit board 60 typically has a plurality of circuit traces (not shown in FIG. 4) interconnecting batteries 37 and circuit component(s) 58. Flexible printed circuit board 60 has at least one flexible hinge or axis of flex 62 which cooperates with cover hinge 56 to provide two substantially parallel and closely adjacent axes or lines of flexibility which together define a flexible connector means comprising a plane or zone of flexibility or flex.

Printed circuit board 60 may be coupled or connected to rigid housing members 52, 54 by any appropriate means eg, an adhesive, snap connectors, rivets, etc. Printed circuit board 60 is coupled to sheet 20 containing reservoirs 23 and 24 by conventional means as described earlier with regard to FIG. 2.

FIG. 5 is an exploded view of another device 100 according to the present invention. Device 100 has a rigid, two-halved upper cover or housing 102. Upper housing 102 comprises two substantially planar, rigid, halves 104, 106 coupled or connected by a flexible compound hinge 108. As with the device 50 of FIG. 4, device 100 has a bolus switch 110 which may be activated by the patient or a medical professional after the device is positioned on the patient's body. Housing 102 also has a peripheral lip which improves the level of comfort experienced by the patient wearing the device. Generally speaking a peripheral lip must have sufficient width to comfortably hold the device against the patient's skin during the full range of body motion without excessively distorting the skin surface to which it adheres so as to cause pain or discomfort.

Device 100 further includes a lower housing 114, and a flexible circuit 116 which sits on lower housing or base component 114. Lower housing 114 comprises two substantially rigid sections, 119, 121 connected by a flexible hinge 123. Flex circuit 116 includes a necked segment 117 which electronically couples its two halves. Positioned over flexible circuit 116 is a battery spacer 120 which holds the batteries (not shown) in position over the battery terminal contacts 118 of flexible circuit 116. Lower housing 114 has a flexible peripheral lip or edge 125 which extends beyond or outside the profile of the device defined by upper housing 102. Such a lip is a preferred construction because it enhances the ability of the device to be held to a patient's skin during drug delivery (eg, by an adhesive) without distorting the patient's skin so as to cause discomfort. Generally speaking, the wide lip must be more flexible than the rigid segments to which it is attached in order to achieve this comfort and conformability objective.

Also of importance in FIG. 5 is the substantial coincidence or planarity of hinge 108 in upper housing 102, necked segment 117 of circuit 116 and the flexible hinge 123 in lower housing 114. These three elements provide flexible physical and electrical coupling between the substantially rigid halves of the device shown in FIG. 5. These elements in combination illustrate a planar flex means or flexible connector means of this invention.

It is well within the design choice of those skilled in this art to determine which of the various assembly components shall be hinged so that physical connection is achieved. For example, the two halves 104, 106 of upper housings 102 may comprise separate pieces if the lower housing 114 and the lower hinge 123 are sufficiently strong so as to retain the physical proximity of the rigid sections of the assembly. Alternatively, upper housing 102 may be comprised of a single hinged piece (eg, halves 104, 106 physically coupled by hinge 108) and lower housing 114 may comprise physically separate sections 119, 121. These design variations are well within the skill of one familiar with this art.

Figure 6:
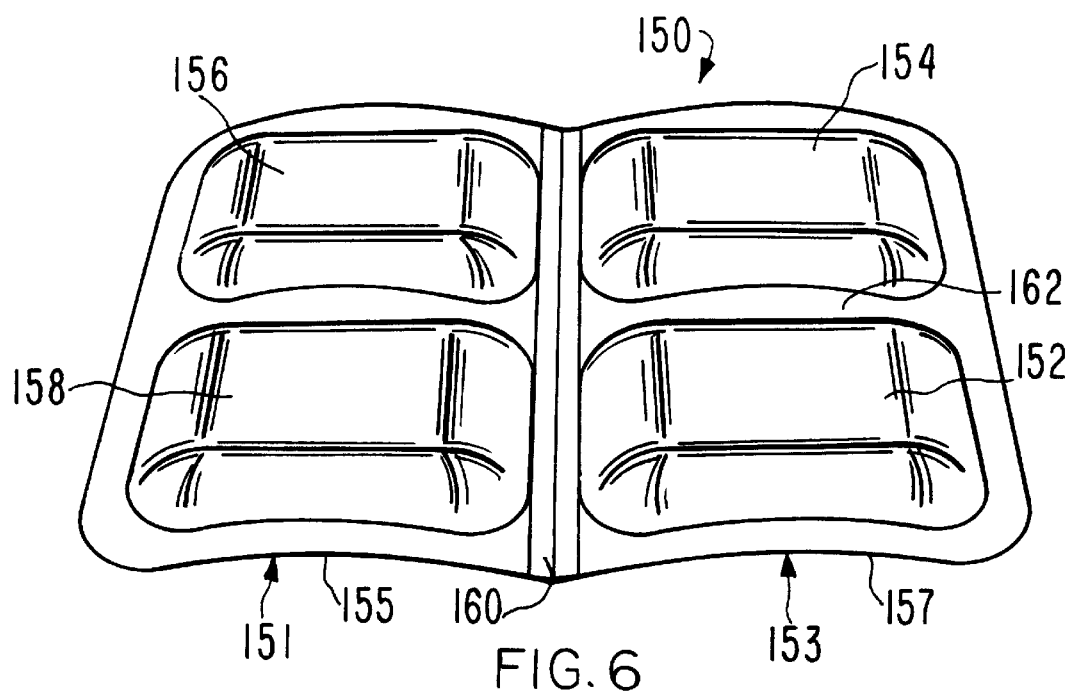
FIG. 6 is a perspective, partial phantom view of another embodiment of the present invention.

FIG. 6 illustrates an embodiment of the present invention in which the electrotransport device 150 has multiple rigid modules 152, 154, 156, 158 and a plurality of flexible connector means or regions 160, 162. Device 150 therefore has two separate and distinct flexible regions 160, 162. The axes of flex of regions 160 and 162 are substantially perpendicular. An array of independent, rigid, but physically connected modules 152, 154, 156, 158 connected by flexible regions 160, 162 is generated.

Of particular note from FIG. 6 is the curved shape of the skin contacting surfaces of electrotransport device 150. As can be seen, flexible region 160 divides device 150 into two rigid segments 151, 153. Each of the segments 151, 153 has a curved skin contacting surface, 155, 157, respectively. The curved (as opposed to planar) surfaces 155, 157 are preferred because many likely device application sites on the body are curved and/or have roughly a cylindrical shape. For example, the arms legs, torso, neck, and fingers all have substantially curved or cylindrical surfaces. A rigid segment 151, 153 having a surface 155, 157 with a radius of cylindrical curvature in the range of 40 to 60 mm is preferred for conforming to the arms of human adults having different body sizes, shapes and physiques. A rigid segment 151, 153 having a surface 155, 157 in the range of about 12 to 18 mm radius of cylindrical curvature is preferred for conforming to the fingers and toes of human adults. A range of about 60 to 90 mm radius of cylindrical curvature is preferred for surfaces conforming to the legs of human adults. A rigid segment 151, 153 having a surface 155, 157 with greater than about a 125 mm radius of cylindrical curvature is preferred for conforming to the torsos of human adults. The radius of a curved, rigid segment is selected substantially to match the smallest body site (eg, torso) sizes encountered in the patient population group to which the device is to be applied. In this manner, the largest possible area of skin contact will result. The resulting enhanced conformity of the device 150 to the body surface, particularly along the edges of the modules 153 and 155, will reduce the likelihood that a module will snag (eg, on the patient's clothing) and peel off the skin during wear. By virtue of the cylindrical, concave underside of surfaces 155 and 157, forces which tend to bias the edges of modules 151 and 153 away from the skin contact surface, which forces are typically observed during the attachment of a flat, single-piece rigid device on the skin of a patient, can be greatly reduced.

By utilization of an array of smaller rigid modules 152, 154, 156 and 158, disposed on a suitably flexible web or sheet (eg, sheet 19 shown in FIGS. 2, 4 and 5), the individual modules can be quite thick and also quite rigid and yet the entire device 150 remains flexible (ie, more able to conform to the natural shape of a body surface). This is due primarily to the presence of flexible regions 160 and 162. This observation is particularly applicable if the rigid modules are adequately separated (eg, by flexible regions 160 and 162) on a flexible connecting "web" or film and the skin contacting surfaces of the modules are curved, angled or radiussed, as depicted in FIG. 6. Generally speaking, it is necessary for any bridge between individual modules be thin and substantially coplanar, otherwise a structure will be produced that will be extremely stiff and non-conformable.

Figure 7:
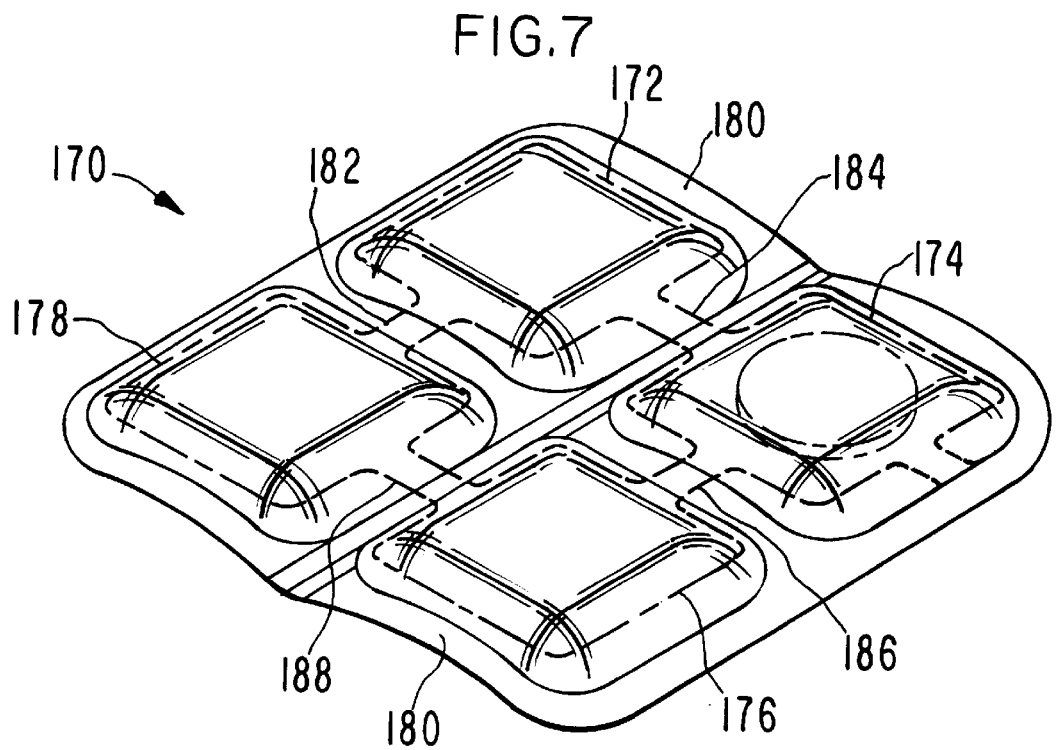
FIG. 7 is a perspective, partial phantom view of the embodiment of the invention shown in FIG. 6 but rotated approximately 45° from the orientation shown in FIG. 6.

FIG. 7 shows a further embodiment of this invention. Device 170 is comprised of multiple rigid modules 172, 174, 176 and 178 which are physically coupled by means of a flexible web 180. This arrangement provides two flexible regions having substantially perpendicular axes of flex. The rigid modules 172, 174, 176 and 178 are also electronically coupled to one another (at 182, 184, 186 and 188) by flexible electronic circuits. In this embodiment the flexible coupling means includes the portion of web 180 between the rigid segments 172, 174, 176, and 178 and circuit couplings 182, 184, 186, and 188 and the underlying sheet (eg, sheet 19) which is not shown in FIG. 7. Like device 150 the individual rigid segments of device 170 are curved or are concave on their skin facing surfaces (eg, their underside surfaces) to enhance skin contact as described above. Web 180 is adhesive on its bottom side to attach sheet 19 (not shown) thereto. The skin contacting surface of sheet 19 is either itself tacky or is coated with a biocompatible skin contact adhesive in order to hold the device 170 in drug transmitting relation to the patient's skin.

Electrotransport devices 150 and 170 illustrated in FIGS. 6 and 7, respectively, demonstrate a further important embodiment of the present invention. The level of comfort experienced by the wearer of a rigid electrotransport system of a certain size may be increased by dividing the overall size of the device into a number of smaller subunits (eg, subunits such as the rigid modules 152, 154, 156 and 158 shown in FIG. 6 or the rigid modules 172, 174, 176 and 178), each of which subunits may itself be rigid as defined herein. However, rather than a single large rigid device, the smaller rigid subunits are interconnected by way of flexible connector means as defined herein. Preferably, the individual rigid subunits have lateral dimensions (ie, lengths and widths as measured roughly parallel to the body surface to which the electrotransport system is applied) in the range of 10–35 mm, more preferably in the range of 15–25 mm. Most preferably, the individual rigid subunits have lateral dimensions within these ranges and also have skin contacting surfaces with radii of cylindrical curvature as described above.

Figure 8:
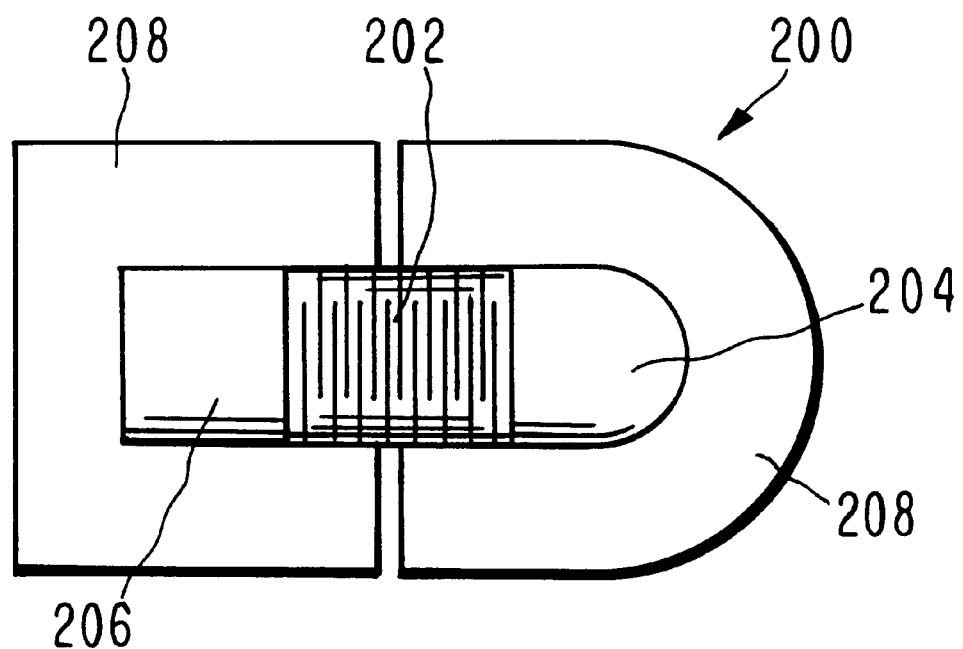
FIG. 8 is a top view of yet another embodiment of the present invention.
Figure 9:
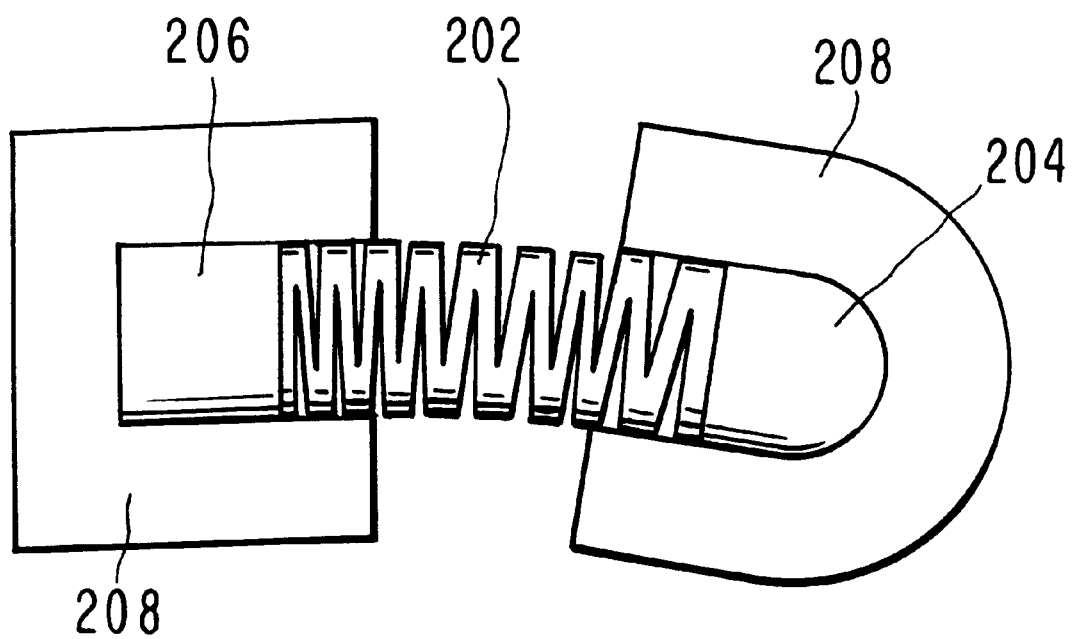
FIG. 9 is another top view of the device shown in FIG. 8 in which the rigid components 204 and 206 have been physically separated.

FIGS. 8 and 9 are top views of another embodiment 200 of the present invention. Device 200 has an "accordion-type" flexible connector means 202, which couples, both physically and electronically, rigid device components 204, 206. As is shown in FIGS. 8 and 9, flexible connector means 202 has a non-extended configuration shown in FIG. 8 and an extended configuration shown in FIG. 9. Thus, device 200 may be placed on a patient's body surface (eg, skin) with webs 208 placed in closely adjacent locations on the body surface. Alternatively, by extending the flexible connector means 202, the webs 208 may be placed in more spaced apart locations on the patient's body surface. As is clearly shown in FIG. 9, the flexible connector means 202 is serpentine shaped. Thus, in the non-extended configuration (FIG. 8), the connector means 202 has a plurality of overlapping portions. These over lapping portions become non-overlapping as the flexible connector means 202 is extended into the more extended configuration shown in FIG. 9. Device components 204, 206 are adhered to the patient's body surface by means of the web 208 which has a biocompatible adhesive on its skin contacting side (not shown). Various web profiles may be employed depending upon the body application site and artistic considerations.

Figure 15:
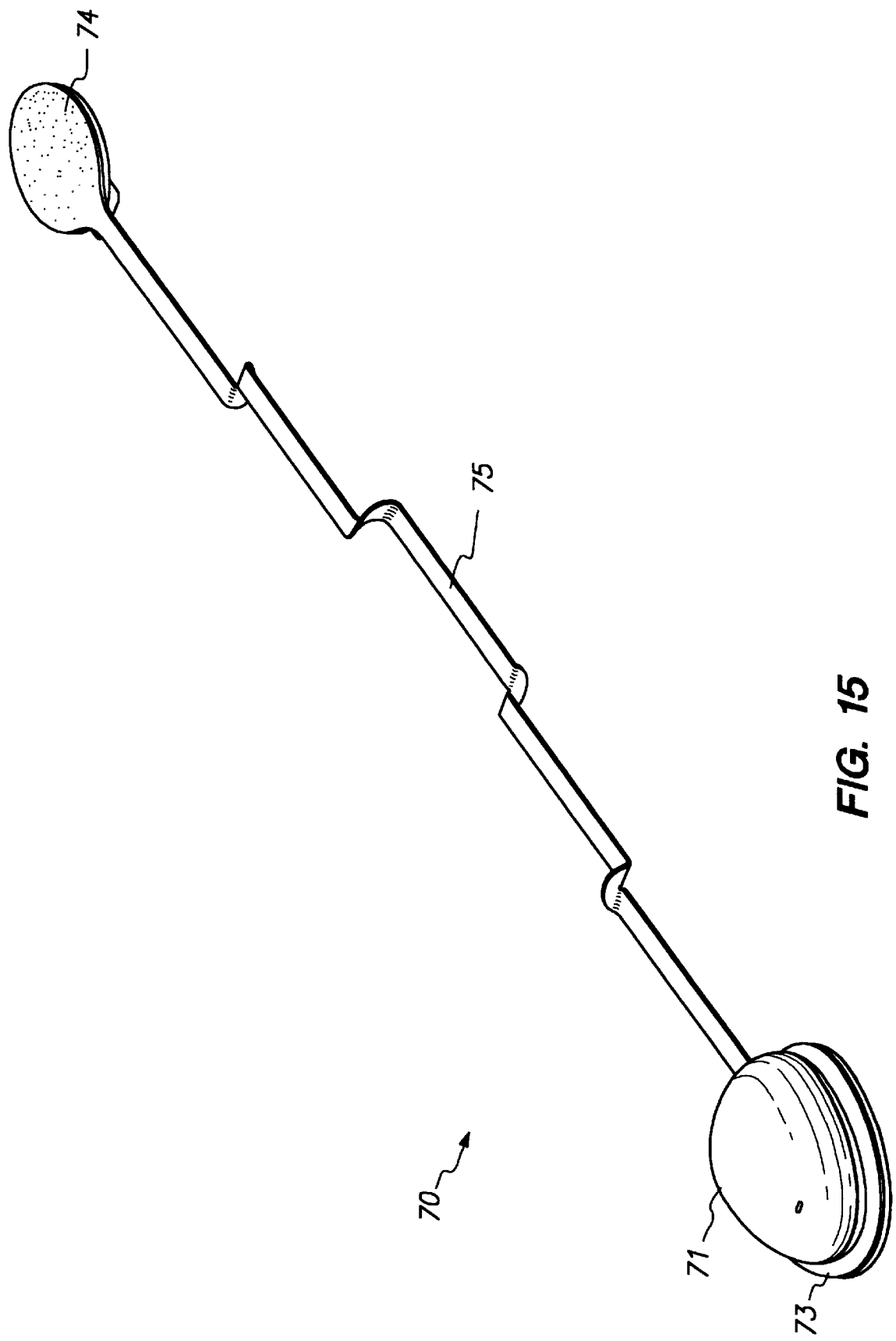
FIG. 15 is a perspective view of the device shown in FIG. 14 with the electrode assemblies in an extended configuration.
Figure 16:
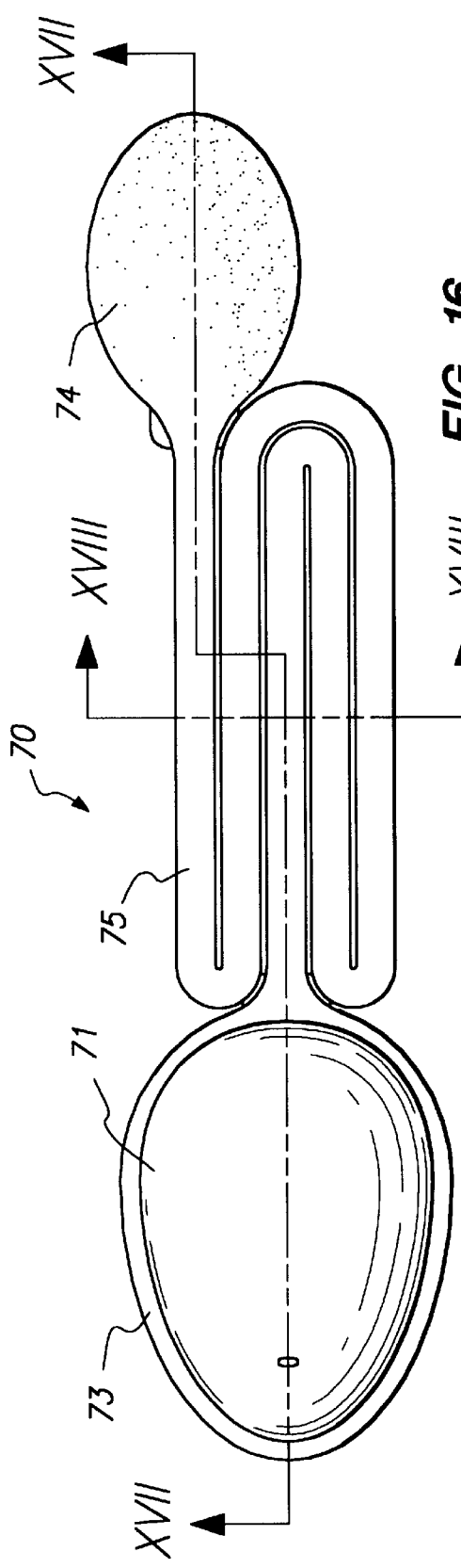
FIG. 16 is a top view of the device shown in FIG. 14.
Figure 17:
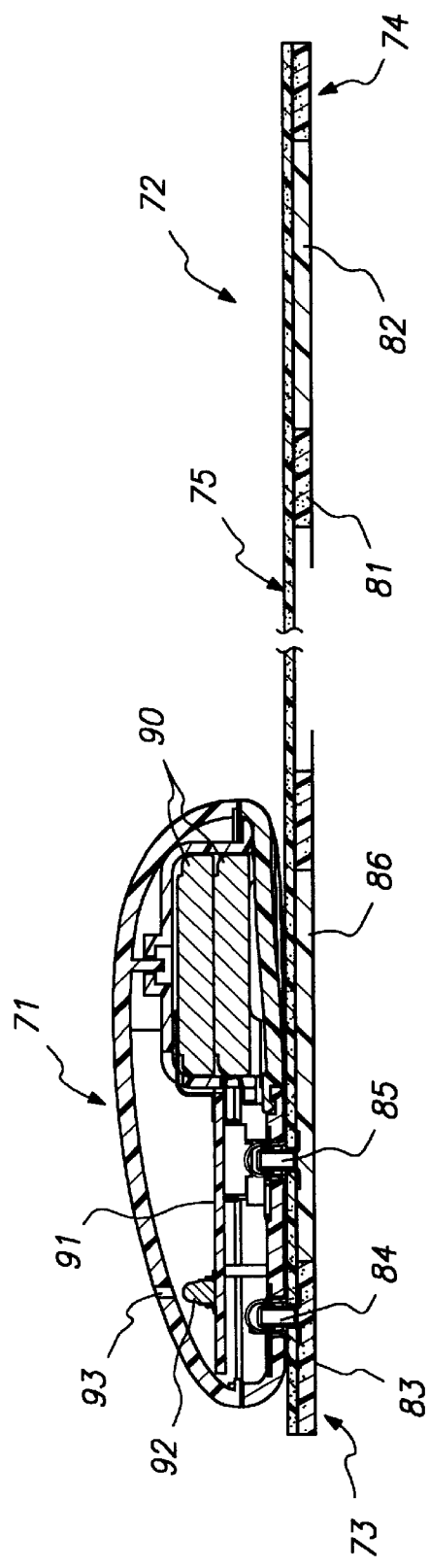
FIG. 17 is a sectional view of the device shown in FIGS. 14–16, taken along line XVII—XVII in FIG. 16.

FIGS. 14 to 18 illustrate another embodiment of this invention. Electrotransport device 70 comprises an electronic controller 71 and a single-use/disposable electrode unit 72. Electrode unit 72 comprises a donor electrode assembly 74 and a counter electrode assembly 73. Unlike other embodiments of the invention described herein, donor electrode assembly may be either rigid, as that term is used herein, or non-rigid. The controller 71 is adapted to releaseably engage electrode unit 72 by means of electrically conductive snap connectors 84, 85 as best shown in FIG. 17. Once the controller 71 engages snap connectors 84, 85, the combined assembly of controller 71 and counter electrode 73 comprises a rigid zone. In accordance with the present invention, electrode assemblies 73 and 74 are physically connected to one another by a flexible means 75. Flexible means 75 has a non-extended configuration (shown in FIG. 14) and an extended configuration (shown in FIG. 15). Thus, device 70 is manufactured with the flexible means 75 having the non-extended serpentine configuration shown in FIG. 14. This configuration allows device 70 to be used on a patient with electrode assemblies 73 and 74 positioned closely adjacent to one another on the patient's body. However, if it is desired to place the electrode assemblies 73 and 74 at more distantly spaced locations on the patient's body, the flexible means 75 may be extended as shown in FIG. 15.

The device 70 with the extendible flexible means 75 is particularly useful in electrotransport devices which are adapted to deliver a drug locally (ie, to a specific body site) as opposed to systemic drug delivery. Examples of locally acting drugs include delivery of local anesthetics for inducing localized anesthesia, delivery of anti-inflammatory agents (eg, NSAID's) for treatment of joint inflammation, delivery of antifungal agents for treating nail fungus, delivery of wart removing agents (eg, salicylic acid) to warts, delivery of anti-tumor drugs to treat skin tumors, delivery of anti-spasmodic agents to treat localized muscle spasms, and delivery of male erection-inducing agents (eg, prostaglandin E1 or papavarine) directly into the penis. One particularly useful application of device 70 is for delivery of local anesthetic agents in order to induce local anesthesia prior to minor surgical procedures, wart removals, mole removals, venipuncture procedures, and in giving hypodermic injections in pediatric applications. For example, if device 70 is used to deliver a local anesthetic agent, such as lidocaine, procaine, bupivacaine, mepivacaine, etidocaine, dibucaine, chloroprocaine, xylocaine, prilocaine, benzocaine, tetracaine, combinations thereof, and mixtures thereof with vasoconstricting agents such as epinephrine and naphazoline, or the like, in order to remove a mole, and the mole is located on the patient's face, it is desirable to attach the counter electrode assembly 73 at a body surface location other than on the patient's face, for example on the upper arm or shoulder. In order to accomplish this, the flexible means 75 is extended by pulling apart the electrode assemblies 73, 74 and a more distant spacing of the electrodes is easily achieved.

Figure 18:
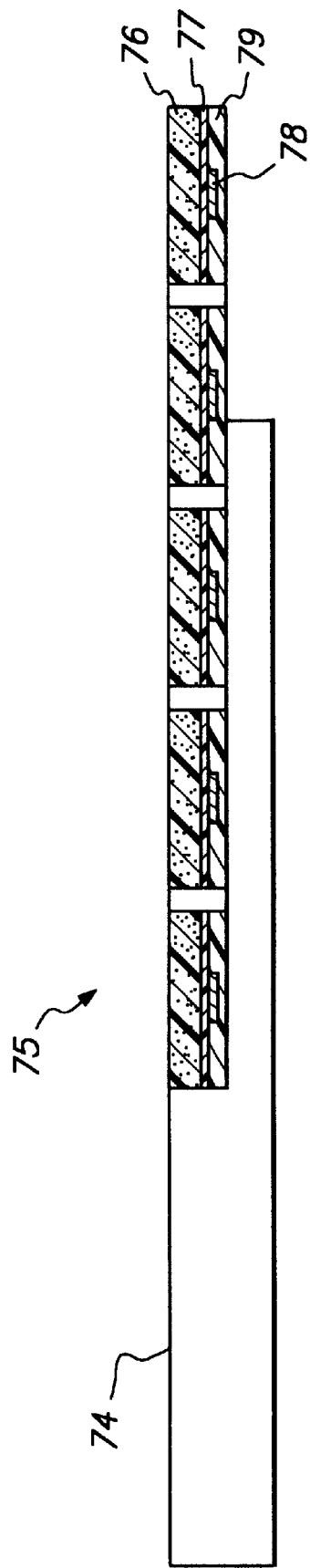
FIG. 18 is a sectional view of the device shown in FIGS. 14–17 taken along line XVIII—XVIII in FIG. 16.

In addition to physically connecting the electrode assemblies 73 and 74, the flexible means 75 has an electrically conductive circuit trace which electrically connects the donor electrode assembly 74 to the controller 71. FIG. 18 shows a sectional view of flexible means 75 taken along lines XVIII—XVIII of FIG. 16. Flexible means 75 comprises a multilaminate structure including a layer 76 of closed-cell polyolefin foam (eg, polyethylene foam having a thickness of 0.8 mm (1/32 inch) and sold by 3M, St. Paul, Minn.) which is coated on one side with a pressure-sensitive (eg, acrylate) adhesive. In addition to closed-cell polyolefin foams, layer 76 can also be composed of fabric (woven or non-woven), or an elastomer (eg, a rubber). On the adhesive coated face of layer 76 is laminated a ink-printable sheet 77, such as Mylar 200D polyester, having a thickness of 0.05 mm (2 mils) and sold by E. I. DuPont DeNemours & Company, Wilmington Del. In addition to polyesters, sheet 77 can also be composed of polyolefins such as polyethylene, or polyvinylchloride. A continuous trace of electrically conductive ink 78 is printed on the polyester sheet 77. Suitable inks include silver, silver chloride and carbon based conductive inks. A particularly preferred conductive ink is sold by Acheson Colloids Co. of Port Huron, Mich. and designated by Model No. SS24381. After printing conductive ink trace 78 on polyester sheet 77, the sheet 77 and trace 78 are coated with an insulating coating 79, providing insulation between the conductive ink trace 78 and the patient. Preferred insulative coating materials are UV curable dielectric coatings sold by Acheson Colloids Co. under the tradenames ML-25094 and ML-25208.

As best shown in FIG. 17, the donor electrode assembly 74 is comprised of a foam layer 81 having a centrally positioned cavity holding a donor reservoir 82. Reservoir 82 preferably comprises a gel holding a solution of the drug or other agent to be delivered by device 70. Similarly, counter electrode assembly 73 is comprised of a foam layer 83 having a centrally positioned cavity holding a counter reservoir 86. Preferably, reservoir 86 contains a solution of a biocompatible electrolyte.

The disposable electrode unit 72 is adapted to be physically and electrically connected to controller 71 by means of snap connectors 84 and 85. Snap connectors 84, 85 may be constructed of metal (eg, stainless steel, nickel-coated brass or silver-coated brass) or metal coated polymers (eg, silver-coated ABS). Snap connector 85 electrically connects the counter electrode assembly 73 to the controller 71 whereas snap connector 84 electrically connects, through conductive ink trace 78, the donor electrode assembly 74 to the controller 71.

Controller 71 contains a pair of serially connected batteries 90 which provide the electrical power for device 70. Controller 71 includes a circuit board 91 having electrical components for controlling the timing and level of the applied current. Circuit board 91 includes an LED 92 which may be viewed through the opening 93 in the controller housing. The LED may be illuminated, for example, when the device is in operation.

Figure 10:
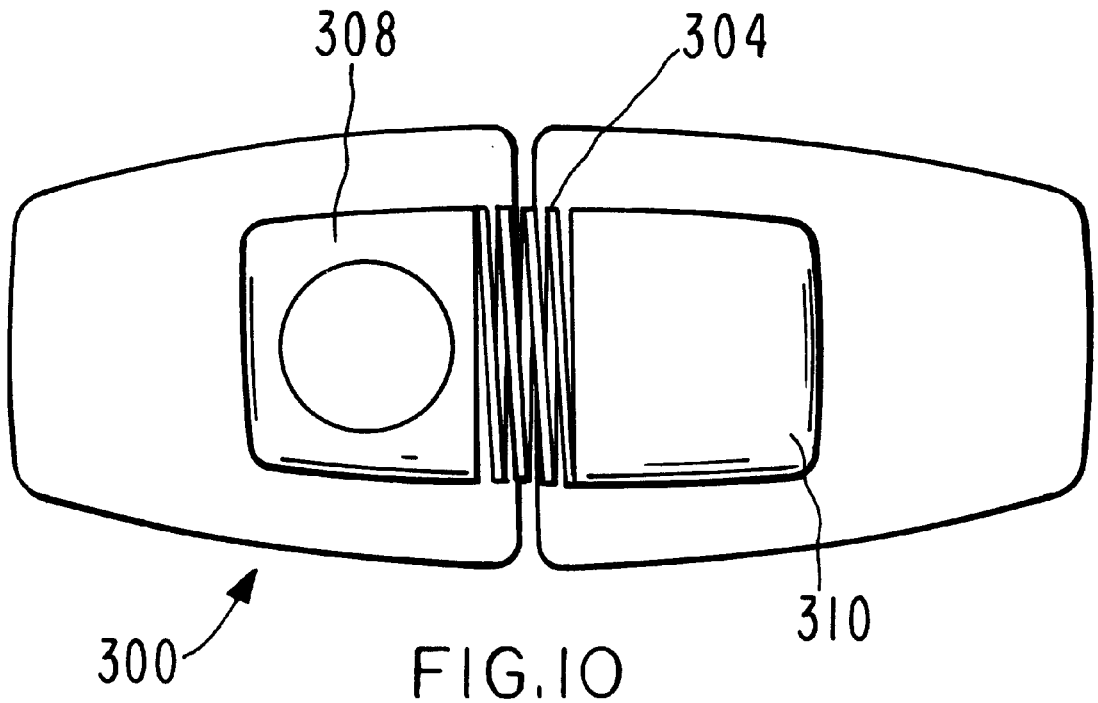
FIG. 10 and FIG. 11 are further embodiments of the present invention.
Figure 11:
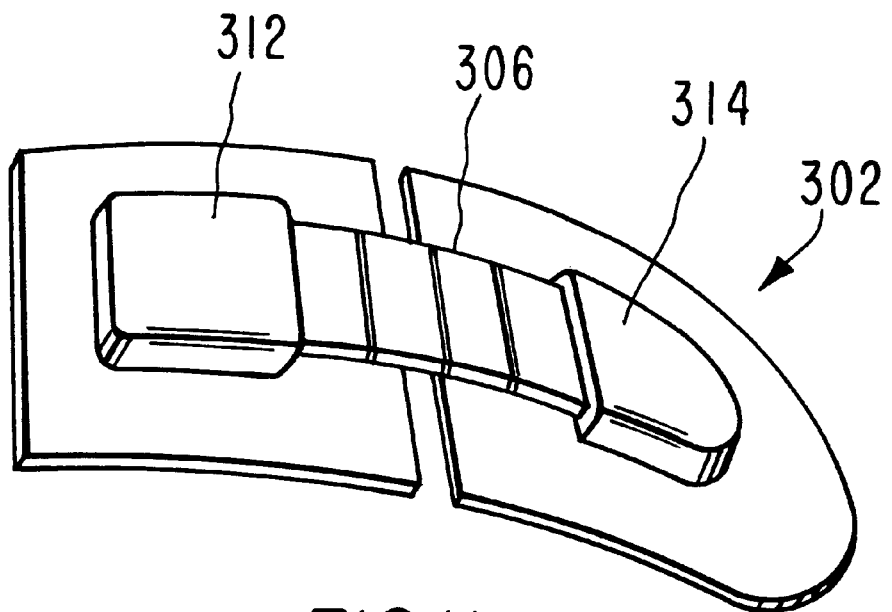

FIGS. 10 and 11 illustrate two further embodiments of this invention. Devices 300 and 302 each have a flexible but non-stretchable connector means 304, 306, respectively, which electronically and physically couple rigid components 308, 310 and 312, 314, respectively. The rigid components may contain batteries or electronic circuit components with no particular significance being attached to which rigid components are included within the respective rigid assemblies. The connector means of FIG. 10 is a plurality of fairly rigid rubber connectors having partial lateral slices projecting inwardly from the edge while in FIG. 11 the connector means is a rubber coated band.

Figure 13:
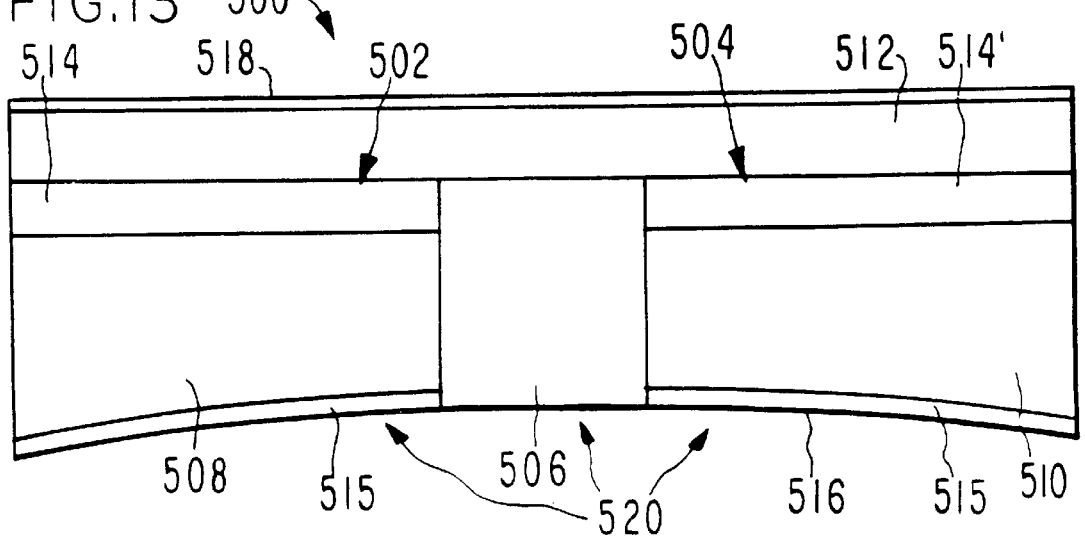
FIG. 13 is yet a further embodiment of the present invention.
Figure 14:
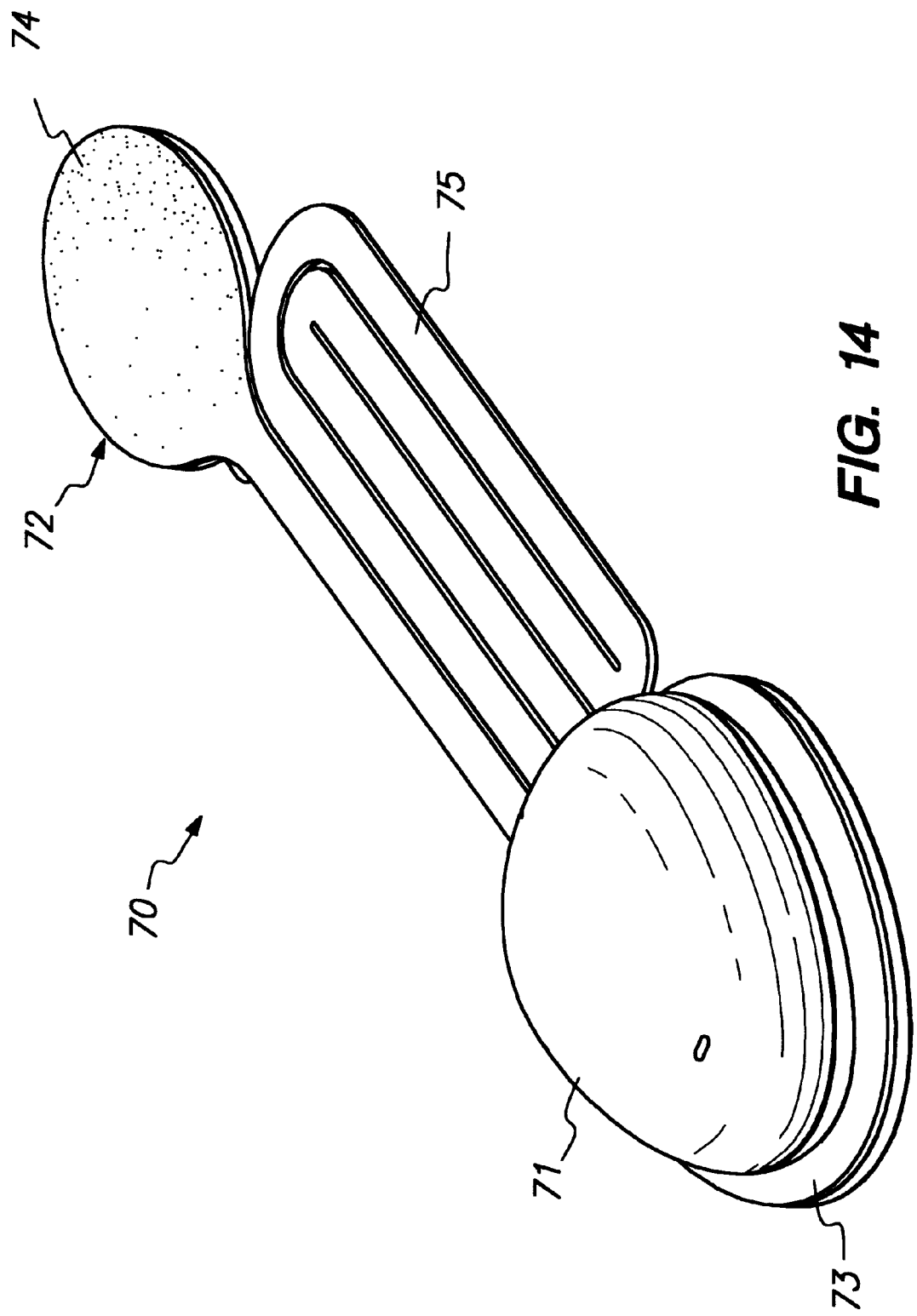
FIG. 14 is a perspective view of a further embodiment of the present invention.

FIG. 13 illustrates a single rigid electrotransport assembly 500 of the invention. A single rigid assembly similar to that of FIG. 13 is described in detail in U.S. Pat. No. 5,158,537, the pertinent portions of which are incorporated by reference herein. Assembly 500 comprises electrode assemblies 502, 504, separated by insulator 506. Electrode assemblies 502, 504 have drug and electrolyte reservoirs 508, 510 and current distribution members 514, 514', respectively. An electronic circuit, which generates and/or controls the electric current applied by electrotranport assembly 500, is electrically connected to current distribution members 514 and 514' and is illustrated schematically in FIG. 13 as layer 512. An optional water-proof backing layer covers layer 512. Agent/ion-conducting adhesive layers 515 are used to hold device 500 to a patient's skin.

Electrotransport assembly 500 has a skin or body proximal side 516 and an exterior or body distal side 518. Body proximal side 516 has a curved configuration (indicated by arrows 520) which enhances the ability of the rigid assembly to adhere to the site of drug delivery, eg an arm, leg or torso, as will be understood. The radius of curvature of body proximal side 516 is adjusted to substantially match the radius of curvature of the body site on which the device is to be attached.

The above-described invention provides a great deal of device design latitude. For example, by utilization of detachable couplers or connectors in conjunction with the flexible connector means, individual device components, or even entire subassemblies may be made detachable. For example, a substantially rigid battery subassembly could be detached from the rest of the electrotransport assembly and replaced when the battery is discharged. Alternatively, a discharged drug source could be detached and replaced (for replenishment) or a different drug (or a different drug concentration) may be substituted.

This invention relates primarily to electrotransport devices having inherently rigid structures or zones. In one practice, zones of an electrotransport apparatus are joined by specialized flexural or flexible membrane structures which allow the rigid elements to be oriented in different planes without peeling away from the patient's skin. This permits the electrotransport device structure as a whole to "bend" or "flex" to conform to cylindrical or even free form geometry, thus maintaining an intimate adhesive contact with the skin.

The invention consists of, in the case of an electrotransport system, a multi-layered (eg, electrode/circuit/drug reservoir/salt reservoir, wicking layer, skin contact, optionally ion-conducting adhesive, and/or electron-conducting adhesive) structure which, because of its novel configuration, remains flexible and conformable to preferred mounting sites on the human body. There are other applications for this structural configuration which will be obvious to those skilled in this field: Skin-mounted infusion devices, skin-mounted passive transdermal devices, diagnostic devices and monitoring devices that should be attached to the skin. The "other applications" have two things (requirements) in common which make them benefit from this invention: (1) the need to be intimately attached to a significant area of skin and (2) the essentially, rigid nature of their structure, which are not compatible requirements.

In this invention, the largest, non-reducible (not able to be broken into sub-modules) element of the system that is structurally rigid and cannot itself be reconfigured to curve-match to the mounting site, can be taken as the standard module size in an array of rigid elements flexibly connected into a conformable, essentially planar structure. In the example of this invention applied to the design of an electrotransport system, the largest rigid element is generally the "button cell" battery. As shown in the figures, the basic module is drawn around the battery, closely enveloping it but presenting a 50 millimeter cylindrical section surface on one side for attachment to the body on sites as small as the 90th percentile female arm and larger. Other modules of identical size may contain other rigid components smaller than the battery. In the example in FIG. 6, four modules are joined to form the flexible array.

Figure 12:
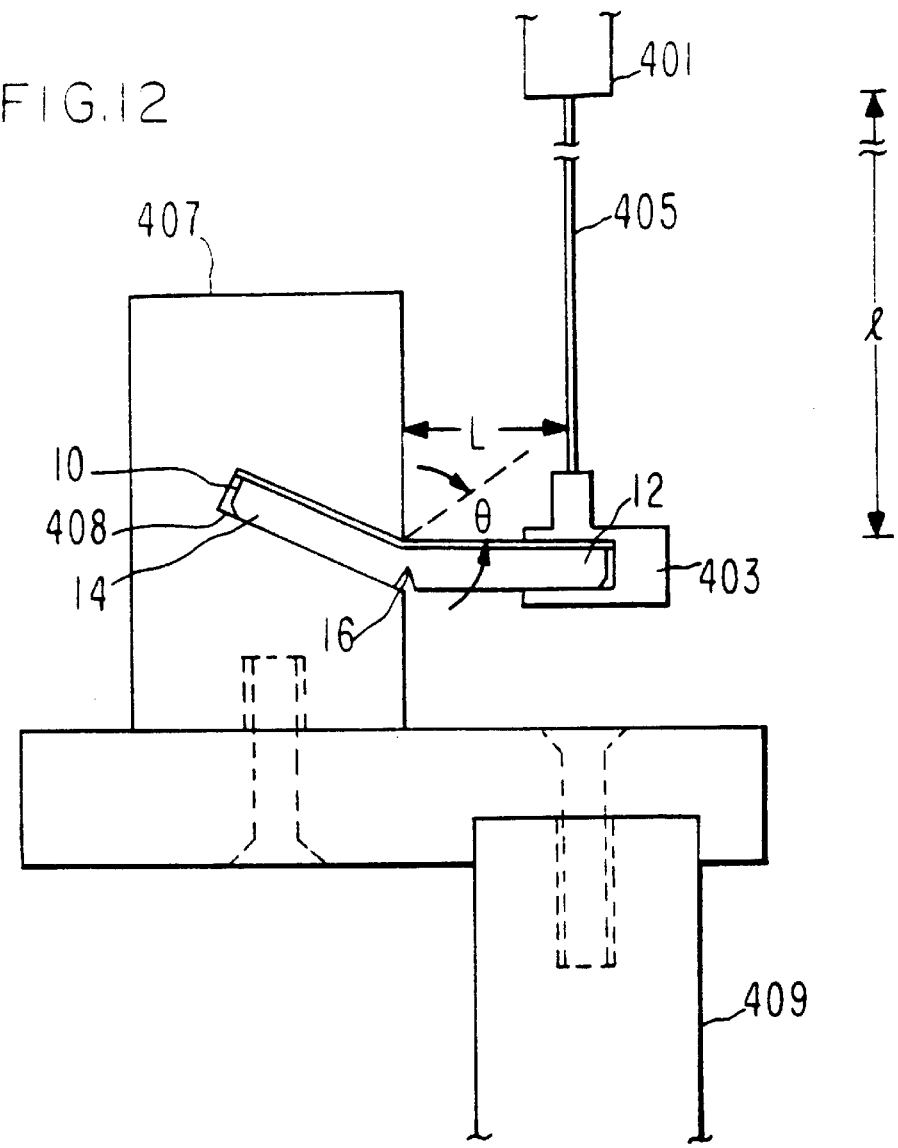
FIG. 12 is a side view of an apparatus for measuring the flexibility and/or rigidity of an electrotransport device or any component thereof.

FIG. 12 illustrates a test fixture for testing the flexural rigidity of an electrotransport system 10 on the Instron stress-strain testing machine Model No. 1122. The tension load cell 401 of the Instron stress-strain testing machine is attached to device 10 by means of a clamp 403 and a cable 405, each of which exhibit minimal (ie, <1%) tensile elasticity (eg, clamp 403 and cable 405 are composed of a metal such as stainless steel). As shown in FIG. 12 the test apparatus is set up to test the flexural rigidity of flexible hinge 16 which is located between rigid housing 12 and 14. In this set-up, clamp 403 is clamped onto rigid housing 12 while rigid housing 12 is at rest in a substantially horizontal orientation. Another clamp 407 holds housing 14 substantially along its width and length right up to the flexible hinge 16. Those skilled in the art will appreciate that the clamp 407 must be custom designed to test a particular system 10. For example, clamp 407 has an opening 408 in which the rigid housing 14 is held. The angle of the axis of opening 408 is determined by the shape of device 10 when device 10 is in a non-flexed (ie, rest) condition. Those skilled in the art will also appreciate that clamp 407 will have an opening 408 with an axis at varying angles to the horizontal depending upon the shape of the particular device being tested. For example, if the electrotransport device had a substantially planer configuration (rather than the slightly bent or V-shaped configuration of device 10) in a non-flexed rest condition, then the axis of opening 408 would be substantially horizontal.

Clamp 407 is securely fastened by conventional means to the moveable cross-head of the Instron stress-strain testing machine. The length (1) of cable 405 is preferably long enough to satisfy the following relation:

$$l/L \leq 10$$

wherein L is the moment arm (see FIG. 12) and I is the distance from the test device to the load cell 401, in order to minimize the effect of the horizontal movement of the clamped end of housing 12 as device 10 flexes around hinge 16.

The flexural rigidity of hinge 16 is measured according to the following procedure. First, the cross-head 409 is moved downwardly to take all slack out of cable 405. Housing 12 should be substantially horizontal at the point where testing is begun. The cross-head 409 is moved downwardly at a cross-head speed of 50 mm/min. causing the rigid housings 12, 14 to bend at an angle θ from the rest position, while the Instron testing machine plots the force-deflection curve. The flexural rigidity, which is the product of the Young's modulus (E) and the moment of inertia (I), is then calculated from the loads and deflection angles measured by the Instron stress-strain testing machine using the following equation:

$$EI = WL^2/2\theta$$

where:
  E=Young's modulus (or modulus of elasticity);
  I=moment of inertia;
  W=the applied load;
  L=the moment arm; and
  θ=the angle of deflection Those skilled in the art will readily appreciate how the apparatus illustrated in FIG. 12 may be modified in order to test the flexural rigidity on one of the rigid housing 12, 14. For example. in order to test the flexural rigidity of rigid housing 14, the housing 12 may be removed (eg, by cutting the system along flexible hinge 16). The rigid housing 14 is then placed within a horizontal opening 408 within clamp 407. A sufficient portion of rigid housing 14 must extend out from clamp 407 in order to enable clamp 403 to be attached hereto.

The terms "agent" or "drug" are used extensively herein. As used herein, the expressions "agent" and "drug" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, anti-depressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary antispasmodics, anticholinergics, antiulceratives, sympathomimetrics, xanthine derivatives, cardiovascular preparations including calcium channel blockers, beta agonists, beta-blockers, antiarrythmics, antihypertensives, ACE inhibitors, benzodiazepine antagonists, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, prostaglandins, proteins, peptides, polypeptides and other macromolecules, psychostimulants, sedatives and tranquilizers.

The present invention can be used to iontophoretically deliver the following drugs: α-2b interferon, alfentanyl, amphotericin B, angiopeptin, atenolol, baclofen, beclomethasone, betamethasone, bisphosphonates, bromocriptine, buserelin, buspirone, buprenorphine, calcitonin, ciclopirox olamine, copper, cromolyn sodium, desmopressin, diclofenac diflorasone, diltiazem, dobutamine, dopamine agonists, dopamine agonists, doxazosin, droperidol, enalapril, fentanyl, encainide, flumazenil, G-CSF, GM-CSF, M-CSF, GHRF, GHRH, gonadorelin, goserelin, granisetron, haloperidol, hydrocortisone, indomethacin insulin, insulinotropin, interleukin, isosorbide dinitrate, ketoprofen,, ketorolac, leuprolide, LHRH, lidocaine, lisinopril, LMW heparin, melatonin, methotrexate, metoclopramide, miconazole, midazolam, nafarelin, nicardipine, nifedipine, NMDA antagonists, octreotide, ondansetron, oxybutynin, $PGE_1$, piroxicam, pramipexole, prazosin, prednisolone, prostaglandins, ranitidine, ritodrine, scopolamine, seglitide, sufentanil, terbutaline, testosterone, tetracaine, tropisetron, vapreotide, vasopressin, verapamil, warfarin, zacopride, zinc, zotasetron.

This invention is also believed to be useful in the iontophoretic delivery of peptides, polypeptides and other macromolecules typically having a molecular weight of at least about 300 daltons, and typically a molecular weight in the range of about 300 to 40,000 daltons. Specific examples of peptides and proteins in this size range include, without limitation, LHRH, LHRH analogs such as buserelin, gonadorelin, napharelin and leuprolide, GHRH, GHRF, insulin, insulinotropin, heparin, calcitonin, octreotide, endorphin, TRH, NT-36 (chemical name: N=[[(s)-4-oxo-2-azetidinyl]carbonyl]-L-histidyl-L-prolinamide), liprecin, pituitary hormones (eg, HGH, HMG, HCG, desmopressin acetate, etc,), follicle luteoids, αANF, growth factors such as growth factor releasing factor (GFRF), βMSH, TGF-β, somatostatin, atrial natriuretic peptide, bradykinin, somatotropin, platelet-derived growth factor, asparaginase, bleomycin sulfate, chymopapain, cholecystokinin, chorionic gonadotropin, corticotropin (ACTH), epidermal growth factor, erythropoietin, epoprostenol (platelet aggregation inhibitor), follicle stimulating hormone, glucagon, hirudin and hirudin analogs such as hirulog, hyaluronidase, interferon, insulin-like growth factors, interleukin-2, menotropins (urofollitropin (FSH) and LH), oxytocin, streptokinase, tissue plasminogen activator, urokinase, vasopressin, desmospressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neuropeptide Y, neurotrophic factors, opiate peptides, parathyroid hormone and agonists, parathyroid hormone antagonists, prostaglandin antagonists, pentigetide, protein C, protein S, ramoplanin, renin inhibitors, thymosin alpha-1, thrombolytics, TNF, vaccines, vasopressin antagonist analogs, alpha-1 anti-trypsin (recombinant).

Generally speaking, it is most preferable to use a water soluble form of the drug or agent to be delivered. Drug or agent precursors, ie, species which generate the selected species by physical or chemical processes such as ionization, dissociation, or dissolution, are within the definition of "agent" or "drug" herein. "Drug" or "agent" is to be understood to include charged and uncharged species as described above.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

We claim:

1. A device for delivering an agent by electrotransport through a body surface, the device having a source of electrical power electrically connected to a pair of electrode assemblies, one of the pair of electrode assemblies having a reservoir for containing the agent to be delivered, the device comprising at least two regions which are placed against the body surface at spaced apart locations and which are held in intimate contact with said body surface, at least one of the two regions being rigid and comprising the power source and an electrode assembly, the regions being physically connected to one another by a connector, the connector having a folded non-extended configuration and an unfolded extended configuration, whereby the regions may be placed on the body surface at: (i) a first set of locations when the connector is in the folded non-extended configuration, or (ii) a second set of locations less proximate that the first set of locations when the connector is in the extended unfolded configuration.

2. The device of claim 1, wherein the first set of locations is more closely spaced than the second set of locations.

3. The device of claim 1, wherein the connector is accordion shaped or serpentine shaped.

4. The device of claim 3, wherein the connector is comprised of a plurality of overlapping portions when in the non-extended configuration, at least some of the overlapping portions becoming non-overlapping when the connector is in the extended configuration.

5. The device of claim 1, wherein the connector is flexible and has a flexural rigidity of less than about $0.75 \times 10^{-3}$ kg-m$^2$/rad.

6. The device of claim 1, wherein the connector is flexible and has a flexural rigidity of less than about $0.45 \times 10^{-3}$ kg-m$^2$/rad.

7. The device of claim 1, wherein at least one of the regions comprises an electronic assembly electrically connected to the power source.

8. The device of claim 1, wherein at least one of the regions consists essentially of an electrode assembly.

9. The device of claim 1, wherein each of the regions comprises an electrode assembly.

10. The device of claim 1, wherein the connector permits angular movement of one region relative to another region.

11. The device of claim 10, wherein the connector permits the regions to deviate from substantial planarity by at least about 15 degrees.

12. The device of claim 1, wherein the connector permits adjustable positioning of one region on the body surface relative to the positioning of another region on the body surface.

13. The device of claim 1, wherein the connector includes an electrical conductor which electrically connects one of the regions to an electrical component in another region.

14. The device of claim 13, wherein the electrical conductor electrically connects an electrode assembly to an electronic controller.

15. The device of claim 13, wherein the electrical conductor comprises an electrically conductive trace.

16. The device of claim 15, wherein the trace is comprised of an electrically conductive ink.

17. The device of claim 1, wherein the connector is comprised of a substrate having an electrically conductive ink trace.

18. The device of claim 17, wherein the substrate comprises a multi-laminate including a layer of foam and an ink-printable polyester sheet.

19. The device of claim 1, wherein the reservoir contains a locally acting agent.

20. The device of claim 1, wherein the reservoir contains an agent selected from the group consisting of local anesthetics, anti-inflammatory agents, anti-fungal agents, wart-removing agents, anti-tumor agents, anti-spasmodic agents and erection-inducing agents.

* * * * *